United States Patent [19]

Ryan

[11] Plant 4,371

[45] Jan. 23, 1979

[54] IMPATIENS PLANT

[76] Inventor: John J. Ryan, 39877 Sundale Dr., Fremont, Calif. 94538

[21] Appl. No.: 875,598

[22] Filed: Feb. 3, 1978

[51] Int. Cl.[2] ..... A01H 5/00
[52] U.S. Cl. ..... Plt./69
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Chippewa, and discovered by me in commercial greenhouses in Fremont, Calif. Chippewa is closest in characteristics to Creek, but has a more upright growth habit; much more floriferous than Creek; both flowers and foliage are lighter than Creek; Chippewa is variegated, depending on light intensity and age of plant; and the candy striping shows on the light pink flowers.

1 Drawing Figure

BACKGROUND OF THE INVENTION

The present new variety (seedling) was discovered by me in a commercial greenhouse in Fremont, Calif., as a result of the cross pollination of the pistil parent Creek (76-2-1) for which a U.S. Plant Pat. No. 4,261 filed 3-28-77 and the unpatented pollen parent 76-13-11.

Asexual reproduction of my new cultivar by terminal or stem cuttings grown in pots in a plastic (polyethylene) greenhouse in Fremont, Calif., under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Chippewa is closest in characteristics to Creek. The following outstanding characteristics of Chippewa distinguish it from Creek.

1. Flowering ability surpasses Creek, but also flowers in pulses (that is, at times has many flowers followed by several weeks with an average number of flowers).

2. Flower color is a lighter shade of pink, candy striping of flower shows U.S. Department of Agriculture Arabesque blood.

3. The growth habit is more upright than Creek, making a better pot.

4. The variegation isn't as wide as in most varieties. As in other varieties light intensity and age increases the width of the variegation. Creek has no variegation. Red pigmentation in the foliage of Chippewa is much lighter than Creek.

DESCRIPTION OF THE PHOTOGRAPH

The accompanying colored photograph illustrates the overall appearance of the cultivar Chippewa showing the colors as true as reasonably possible for this type of colored reproduction. However, under low light and cool temperatures the flower color darkens and the variegation width decreases; under high light and temperatures the flower color lightens and the variegation width increases.

DETAILED DESCRIPTION

The following detailed description of Chippewa was based on observations made of the new cultivar on Nov. 1, 1977.

I. Plant:

*Name.*—Chippewa.

*Origin.*—Seedling of the cross pollination of the pistil parent Creek (76-2-1) U.S. Plant Pat. No. 4,261, filed 3-28-77 and the unpatented pollen parent 76-36-11.

*Form.*—Upright.

*Height to flowering.*—38 cm. to 45 cm.

*Growth.*—Fast.

*Type of cutting.*—Terminal or stem.

*Rooting time.*—Typical, 10–14 days.

*Rooting habit.*—Fast, dendritic.

II. Foliage:

*Arrangement.*—Lower leaves of any break opposite (usually one set); upper foliage of any break whorls of 3 to 6.

*Shape.*—Generally elliptical.

*Tip.*—Acuminate.

*Base.*—Attenuate.

*Margin.*—Serrulate.

*Veination.*—Pinnate.

*Size.*—Blade and petiole 11.5 cm. to 18.5 cm; length of blade 9.5 cm. to 14.0 cm.; width at widest point 3.0 cm. to 5.0 cm.

*Surface.*—1. Texture: Glabrous, typically waxy. 2. Smoothness: Leaf cupped down.

*Variegation.*—High light and age of cutting increases variegation; whereas low light and high fertilization reduces variegation and increases leaf size.

*Color.*—1. Petiole: a. Upper 185 B. b. Lower 185 A. Older leaves have darker petiole color. 2. Veins: 185 B. 3. Leaf: a. Upper 137 A. b. Lower 138 B. 4. Variegation: a. Edge 137 B. b. Middle 137 B to 8 C (very gradual change). c. Center 8 C.

III. Stem:

*Color.*—In new growth fairly red (185 A), but loses color rapidly with age.

*Internode.*—1. Length: Short to moderate. 2. Size: Moderate.

*Node expanded (relative to internode).*—Larger than internode.

*Breaking action.*—Good.

IV. Flower:

*Form.*—Typical.

*Borne.*—End of branches, terminal.

*Blooming habit.*—1. Relative number: Above average. 2. Time to flowering: Average. 3. Longevity: Typical, 3-5 days.

*Size of mature flower.*—First flower on a plant may be small. 1. Length: 5.5 cm. to 6.0 cm. 2. Width: 5.5 cm. to 6.0 cm. 3. Spur: 4.5 cm. to 5.0 cm.

*Color.*—Lighter pink under high light and heat.

| | | |
|---|---|---|
| 1. | Eye: | 58 C |
| 2. | Middle | Candy stripes 43 C; rest of petal 36 D |
| 3. | Edge | |
| 4. | Pedicel: | 4 D |

V. Reproductive organs.

*Stamen.*—

| | | |
|---|---|---|
| 1. | Anthers | Typical, Fused hood over pistil |
| 2. | Filaments | |
| 3. | Pollen | |
| a. | Color: | 18 C |
| b. | Abundance: | Typical, plenty |

*Pistils.*—

| | | |
|---|---|---|
| 1. | Style | Typical |
| 2. | Ovaries | |

VI. Other characteristics: As with a few other varieties, it definitely flowers in pulses.

I claim:

1. A new and distinct form of Impatiens plant as described and illustrated, known by the cultivar name Chippewa, that has variegation depending on light intensity and age of cutting; a candy striped light pink flower; many flowers; a very upright growth habit; and a slight foliar reddening.

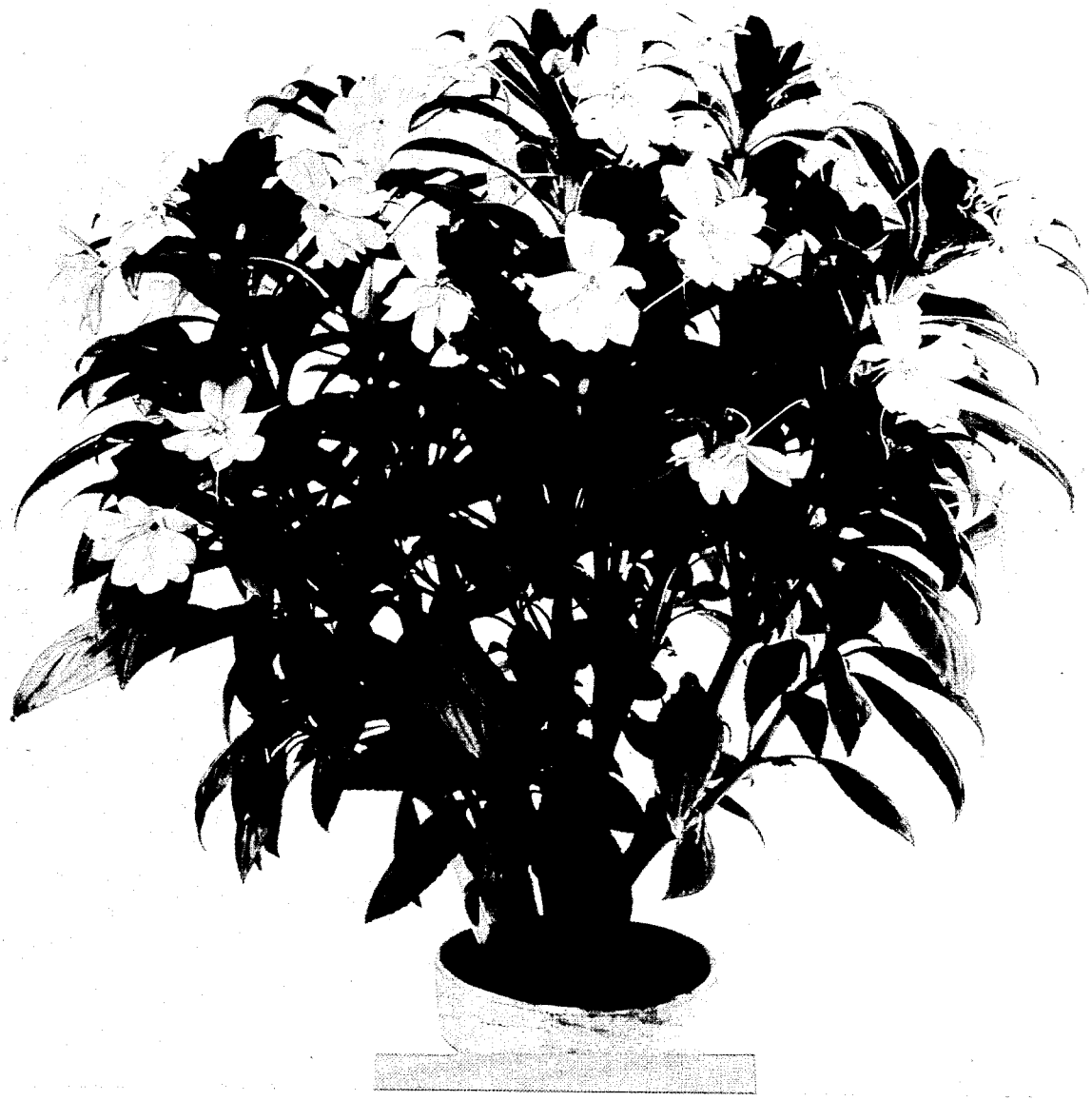

* * * * *